United States Patent [19]
Chilcott

[11] Patent Number: 4,946,276
[45] Date of Patent: Aug. 7, 1990

[54] FULL ROLL FINGERPRINT APPARATUS

[75] Inventor: William J. Chilcott, Ossining, N.Y.

[73] Assignee: Fingermatrix, Inc., North White Plains, N.Y.

[21] Appl. No.: 248,435

[22] Filed: Sep. 23, 1988

[51] Int. Cl.⁵ .............................................. G06K 9/20
[52] U.S. Cl. ................................................... 356/71
[58] Field of Search ........................... 356/71; 382/4, 5

[56] References Cited

U.S. PATENT DOCUMENTS

| | | | |
|---|---|---|---|
| 3,527,535 | 9/1970 | Monroe | 356/71 |
| 3,975,711 | 8/1976 | McMahon | 356/71 |
| 4,537,484 | 8/1985 | Fowler et al. | 356/71 |
| 4,553,837 | 11/1985 | Marcus | 356/71 |
| 4,783,167 | 11/1988 | Schuller et al. | 356/71 |

Primary Examiner—Richard A. Rosenberger
Attorney, Agent, or Firm—McAulay Fisher Nissen & Goldberg

[57] ABSTRACT

As a live finger is rolled across a glass platen in an optical scan fingerprint apparatus, a series of lights turn on and off to demarcate the line along the platen at which the optical scan is being taken. In this fashion, the finger applied to the platen can be rotated across the platen at a rate that keeps sufficient track with the scan to provide a complete (nail-to-nail) full roll scan.

8 Claims, 4 Drawing Sheets

FULL ROLL FINGERPRINT APPARATUS

BACKGROUND OF THE INVENTION

This invention relates generally to a fingerprint processing apparatus and more particularly to one that is capable of generating a full roll fingerprint image by means of an optical scanning technique.

Optical scan finger image processing apparatus capable of generating a fingerprint image that can be encoded into machine readable signals are known in the art. Examples of such apparatus are described in U.S. Pat. Nos. 4,553,837, 4,544,267, 4,537,484, 4,322,163 and 4,152,056. These patents indicate techniques for providing an optical scan of a finger held against a transparent platen in which an interrogating light beam is scanned across the finger to provide a reflected modulated light beam which is focused onto an array of photo-electric transducers to provide a series of electrical signals that carry fingerprint information. Some of these patents use a flat platen. Others used a curved platen in order to get a larger portion of the fingerprint than a flat platen provides.

It is often desired to provide an optically developed fingerprint that is a full roll fingerprint of the sort that is obtained by rolling a finger across an ink pad from nail edge to nail edge and then rolling the inked finger across a card.

In order to provide as much finger contact as possible on the concave surface of the curved platen, the optical fingerprint apparatus may employ multiple curved platens having different dimensions to accommodate fingers of different thickness and different nominal radius. Yet, even with multiple diameter curved platens, a finger that fits within the closest approximation will not fully touch from nail to nail. The reasons for this in part are because the range of finger sizes are continuous while the number of curved platens that can be provided are limited and in part because the finger surface is not a perfect circular cylinder.

Accordingly, the purpose of this invention is to provide a technique and an apparatus to permit obtaining a full nail-to-nail roll fingerprint from an optical scanning apparatus employing a platen.

A related purpose of this invention is to provide this full roll technique with a mechanism that is sufficiently simple and straightforward in use so that it will provide accurate results on a consistent basis with a large number and wide variety of fingers.

It is important that the apparatus takes into account not only the variability of the population of fingers but also the variable ability of people to interface with a machine.

BRIEF DESCRIPTION

In one embodiment of this invention, a finger is rolled over the touching surface of a flat or curved platen while the optical scan is being taken. Because the contact area of even the smallest finger on a flat platen is substantial, the synchronization between the state of the rotation of the finger along the platen surface and the position of the scan line need be only approximate. As long as the finger is in its initial position before the scan starts and is in its final position before the scan ends, a complete "nail-to-nail" full roll scan can be taken.

Accordingly, the individual whose fingerprint is being taken, or the individual controlling the finger rotation or finger movement, can essentially eyeball the scan in order to maintain adequate tracking. In order to make such eyeballing of the tracking between finger position and scan feasible, an eight lamp LED display is lit in electrical synchronization with the position of the scan. In the position of the finger when it is rolled to the start of scan, all of the lights are turned on. As the scan proceeds, lights one at a time are turned off to indicate the position of the scan in eight equal segments. This provides the visual cues necessary to assure that the finger is voluntarily moved in sufficient track with the scan line so that it neither runs ahead nor lags behind the scan. Because of the large angular contact of the finger around the scan line, the eight light cues provided are sufficient to assure that the finger adequately tracks with the scan.

BRIEF DESCRIPTION OF THE DRAWINGS

FIG. 2 shows those lights which are lit at the stage illustrated. At prior to the start of the scan, all of the lights are off (b) and all are turned on as the scan starts (c).

DESCRIPTION OF THE PREFERRED EMBODIMENTS

Figure 1:
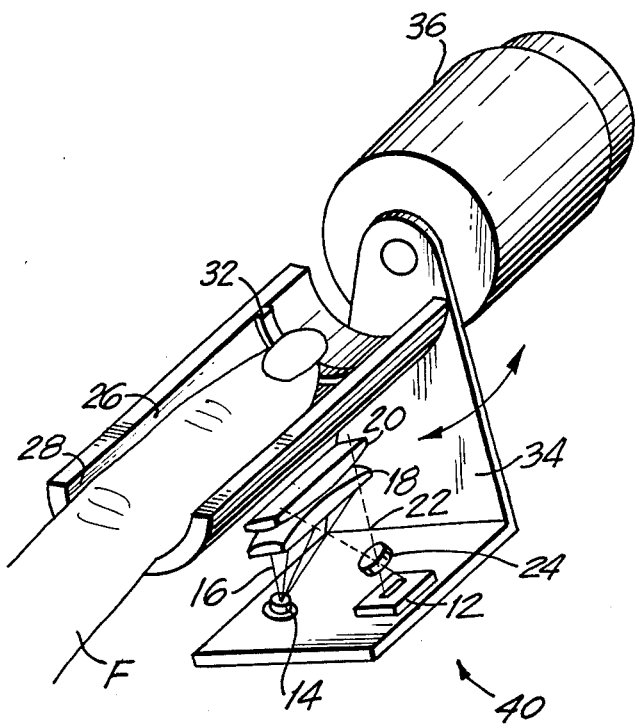
FIG. 1 is a perspective view of a first fingerprint processing apparatus with which the present invention may be used.
Figure 2A:
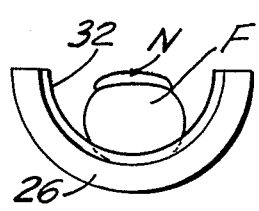
FIGS. 2(a)–2(e) are schematic illustrations of a finger F on the FIG. 1 cylindrical platen showing: (a) finger placement prior to the start of the scanning operation, (b) the finger rolled to a start of scan position, (c) the start of the scan, (d) the finger rolled halfway back along the platen after the start of scan, and (e) the finger rolled along the platen to the end of the optical scan.
Figure 2B:
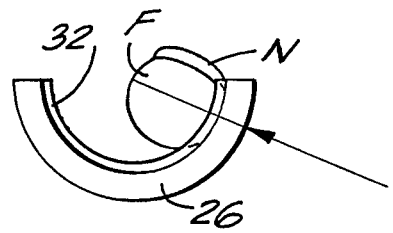
Figure 2C:
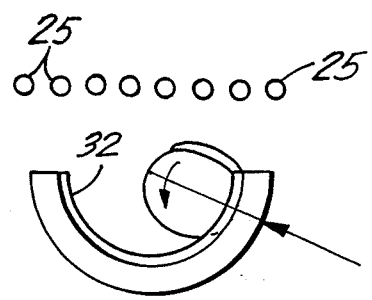
Figure 2D:
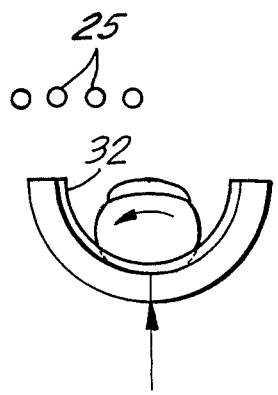
Figure 2E:
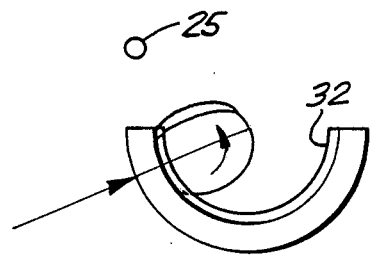
Figure 3A:
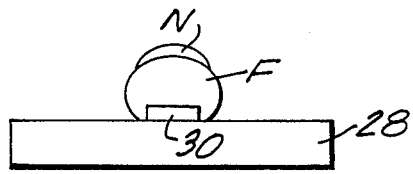
FIG. 3(a)–3(e) are schematic illustrations similar to that of FIGS. 2(a)–2(e) showing the sequence finger positions on a flat platen.
Figure 3B:
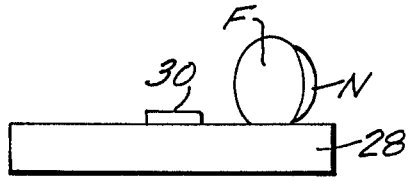
Figure 3C:
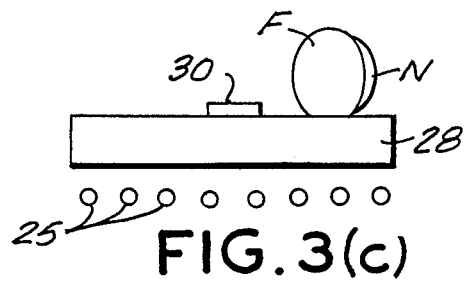
Figure 3D:
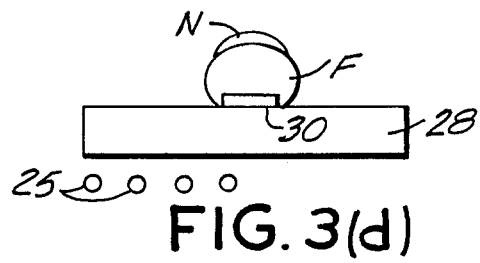
Figure 3E:
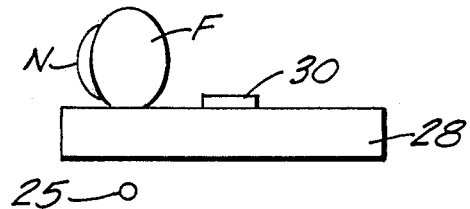

FIG. 1 illustrates a fingerprint apparatus that is disclosed in U.S. Pat. No. 4,553,837 and that represents one embodiment with which the device of this invention may be employed. Since the operation in FIG. 1 is disclosed in said patent, all that need be pointed out here is that a laser 14 provides a light beam 16 which is shaped by cylindrical lenses 18 and 20 to form an interrogating light beam that is substantially in the form of a slit light beam running the length of the forward portion of the finger F. The finger F is on the concave surface of a transparent glass platen 26 that is in the form of a semi-cylinder. A stop 32 aids in positioning the finger longitudinally. The reflected light beam is modulated to contain fingerprint information and is focused by lens 24 onto an array 12 of photo-responsive transducers. The entire optical system except for the platen 26 is mounted on a bracket 34 which is mounted to the axis of the motor 36 so that the optical system can rotate about the approximate axis of the finger F to provide a more extensive fingerprint than would be available if the platen 26 were a flat platen.

As can well be imagined from the FIG. 1 showing, a typical finger will not entirely mesh with the concave touching surface of the platen 26. Even though a number of different platens having different nominal diameters may be used, the variety of finger sizes is so great that there would not be congruence between the exterior of the finger and the touching surface of the cylindrical platen 26. In addition, the typical finger is not perfectly cylindrical and a portion of the finger that is not near the nail edges is not going to touch the platen involved.

Accordingly, a more desirable routine for having the entire finger, from nail edge to nail edge, contact the platen surface is to have the finger rotated along the platen surface during the course of the scan. It is important that the finger be rotated to track with the scan and to neither run behind the scan nor ahead of the scan. This is done by virtue of a set of lights, specifically the LEDs 25 shown in FIG. 2, which may be conveniently arranged at any location visible to the individual whose fingerprint is being taken or to the individual administering the fingerprint operation.

The scan normally takes two seconds. A substantial portion of the finger surface is in contact with the concave surface of the platen 26 at any position of the finger rotation along the platen. Thus, precise synchronization between angular finger position and scan position is not necessary. However, adequate track between finger rotational position and scan position, is obtained by rotating the finger in accordance with the turning off of the series of eight lights 25 that divide the scan into seven equal angular portions. This can be done visually. The lights 25 give an adequate visual cue to the administrator for the rotational position of the fingerprint involved.

FIG. 2 illustrates five steps in sequence of the application of a finger F to a curved platen 26 in accordance with the method and apparatus of this invention. As shown at 2(a), the finger F is placed with the finger surface down and the nail N up in the center of the platen 26. A stop 32 is located on the platen 26 to position the finger longitudinally. This assures that the finger F is within the geometry of the scan of the scanning mechanism. FIG. 2 is an end view of the finger F on the platen 20 and the stop 32 is in front of the end of the finger F.

The finger is then rolled clockwise as seen from the end of the finger to the position as shown at 2(b). In this position, a first end of the nail N is either in contact with the platen 26 or nearly in contact. At this point, the operator initiates the scan and all of the lights 25 are turned on as indicated at 2(c). The turning on of the lights 25 provides a visual cue that the scan has started and thus the finger can start rotating in a counter-clockwise direction as seen from FIG. 2. As the scan proceeds, individual lights 25 are turned off in synchronism with the position of the scan. This provides a continuous visual cue to facilitate having the finger F rotated in track with the scan or at least in sufficient track with the scan so that there is substantial amount of finger surface on either side of the scan line at any moment during the scan.

Thus, as seen at 2(d), about half of the lights 24 are turned off by the time the finger comes back to the center initial position. The lights 25 continue to be turned off until, as shown at 2(e), a finger is at a second nail edge end position. At this point, one of the lights 25 is still on indicating that the scan is continuing. After the scan has been completed, the last light 25 turns off and the finger can then be removed from the platen.

Alternatively, the lights 25 can be turned on, one at a time, in track with the scan in order to provide a moving point indicator to the individual using the apparatus as to the proper rotational position of the finger being scanned.

FIG. 3 is a schematic illustration similar to that of FIG. 2 but showing the finger placement positions on a flat platen 28. The five positions (a) through (e) shown in FIG. 3 correspond to the five positions (a) through (e) shown in FIG. 2. In the FIG. 3 arrangement, the flat platen 28 has a stop 30 which aids in positioning the finger F, not only longitudinally, but also in terms of centering it on the flat platen 28. Similar to the technique discussed in connection with FIG. 2, the finger F is initially placed as shown at 3(a) along the center of the platen 28 against the stop 30. The finger is then rotated counter-clockwise to a first end position 3(b) with the nail N essentially abutting against the platen 28. At this position, when scan starts, all eight of the LEDs 25 light up as shown at 3(c) and the finger F is then caused to rotate clockwise and keeps track with the LEDs 25 as they turn off one by one. The LEDs 25 turn off one by one in synchronism with the optical scan and the finger F tracks with the lights 25 as they turn off by visual tracking. At the halfway point of the scan, as shown at 3(d), half the lights are off. At the end of the scan, as shown at 3(e), a single light 25 is left on so that the finger will be kept in place until the scan is completed. When the scan is completed and the last light 25 turns off, the finger F is removed.

The flat platen arrangement illustrated in FIG. 3 requires that the scan line (and thus the slit light beam) extend across the platen 28 along a line approximately parallel to the axis of the finger. This differs from the showing in U.S. Pat. No. 4,322,163 where the scan line (and thus the slit light beam) extends laterally across the finger and is traversed longitudinally.

Figure 4:
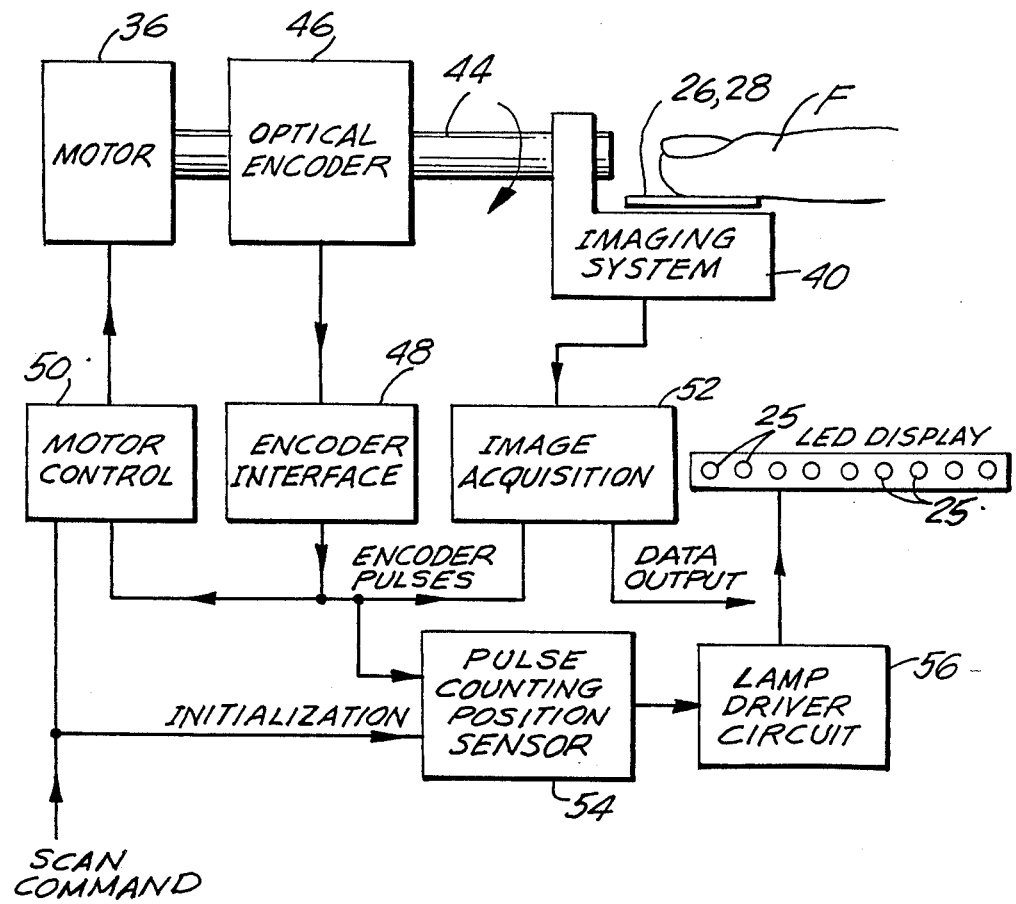
FIG. 4 is a block diagram illustrating the control circuitry that relates the LED display to the state of the scan and thus the position of the finger being scanned.

FIG. 4 illustrates the circuit arrangement for synchronizing the output of the LED display 25 to the scanning position. A finger F is placed on a stationary platen such that an imaging system 40 can be rotated around the platen if the platen is curved, or moved along a plane under the platen if the platen is flat. The imaging system comprises the other light source and lenses and photo-transducers such as shown in FIG. 1 and described in U.S. Pat. No. 4,544,267 in connection with the flat platen or in U.S. Pat. No. 4,553,837 in connection with a curved platen.

A motor 36 drives the shaft 44 which rotates the imaging system. An optical encoder 46 coupled to that shaft 44 provides an output signal through an encoder interface 48, to indicate shaft angle position. The motor 36 is controlled by a motor control unit 50 with an internal clock. A scan command initiates scan. Shaft angle position information from the encoder 46, 48 is applied to the image acquisition functions 52 so that the image which is developed from the transducers and initially processed is appropriately correlated to the scan position and the data output is thereby properly ordered and identified. The interface 48 output pulses also operate to provide speed control of the motor 36.

For the purpose of this invention, the important point about FIG. 4 is that the initiation of scan command is also applied to a pulse counter 54 together with the shaft angle pulses. If we assume that during a single scan approximately 2,000 encoded pulses are generated, then the pulse counter 54 provides an output signal once each 250 pulses. An output from the pulser 54 is applied to the lamp driver circuit 56 at the initiation of the scan command so that the display of eight LEDs 24 are all turned on. Then after each count of 250 pulses by the pulser 54, an output from the pulser 54 turns off one of the LEDs 25.

It should be noted that what is being done is to keep track with the scan line. The scan line is the line interrogated by the photoelectric transducers. For reasons of operating efficiency, the design as shown in FIG. 1, uses a thin optical beam that is rotated across the platen. But one could simply flood the platen with light and scan across the finger along with the lens 24 and array 12 of photo responsive transducers. It should be understood that the scan referred to herein is that scan of the modulated light beam. It does not necessarily mean that the interrogated light beam itself necessarily physically moves or physically scans.

What is claimed is:

1. In an optical scan fingerprint apparatus having an interrogating light beam that illuminates a finger object on a platen to provide a reflected modulated light beam having finger surface information that can be focused to provide a fingerprint image, the improvement to provide a full roll fingerprint image comprising:
   a plurality of sensory indicia,
   synchronizing means to change the state of said indicia as a function of the position of the optical scan,
   whereby a finger that is rolled on said platen in track with the changing state of said indicia will track with the scan.

2. The improvement of claim 1 wherein:
   said indicia are a set of indicating lights and said synchronizing means serves to set all of said lights in a first state at the beginning of scan and to change the state of each of said lights to a second state in a sequential fashion as the scan proceeds.

3. The improvement of claim 2 wherein the state of all of said lights has been changed to the second state by the end of scan.

4. The improvement of claim 1 wherein said synchronizing means turns on all of said lights at the beginning of the scan and turns the lights off one at a time as the scan proceeds until all of the lights have turned off by the end of scan.

5. In the method of optically scanning a finger object to provide a modulated light beam having finger surface information that can be focused as a fingerprint image, the improvement to provide a full roll fingerprint image comprising the steps of:
   positioning the finger on the platen,
   rolling the finger to a first end position in which a first nail edge end of the full roll fingerprint is applied to the platen,
   initiating the optical scan,
   sequentially changing the state of each of a plurality of sensory indicia in synchronization with the optical scan,
   rolling the finger on the platen to a second nail edge end position,
   said step of rolling the finger over said platen between one nail edge end position to the other nail edge end position being taken in track with the change of state of said sensory indicia.

6. The method of claim 5 wherein:
   said sensory indicia are a set of indicating lights, and
   said step of sequentially changing the state of said lights sets all of said lights in a first state at the beginning of scan and changes the state of each of said lights one at a time to a second state in sequential fashion as the scan proceeds.

7. The method of claim 6 wherein the state of all of said lights is changed to the second state by the end of scan.

8. The method of claim 6 wherein said step of sequentially changing the state of said lights turns on all of said lights at the beginning of the scan and turns the lights off one at a time as the scan proceeds until all of the lights are turned off by the end of the scan.

* * * * *